United States Patent [19]

Dickneite et al.

[11] Patent Number: 4,699,912
[45] Date of Patent: Oct. 13, 1987

[54] USE OF LYCORINE AS AN IMMUNOSUPPRESSOR

[75] Inventors: Gerhard Dickneite, Marburg-Cappel; Hans-Ulrich Schorlemmer, Weimar; Hans-Harald Sedlacek, Marburg, all of Fed. Rep. of Germany

[73] Assignee: Behringwerke Aktiengesellschaft, Fed. Rep. of Germany

[21] Appl. No.: 754,269

[22] Filed: Jul. 12, 1985

[30] Foreign Application Priority Data

Jul. 16, 1984 [DE] Fed. Rep. of Germany ....... 3426109

[51] Int. Cl.⁴ ............................................. A61K 31/44
[52] U.S. Cl. ..................................... 514/283; 514/885
[58] Field of Search ................................. 514/283, 885

[56] References Cited

PUBLICATIONS

E. F. Steinmetz, "Codex Vegetabilis", Item 746, (1957).
The Merck Index, 10th ed., Item 5442, (1983).
Chemical Abstracts, vol. 80, p. 18, No. 103858s, 1974.
Berenbaum, Immunology, 36:355–365, (1979).
Ehrke et al., Int. J. Immunopharmac., 5:43–48, (1983).

Primary Examiner—Albert T. Meyers
Assistant Examiner—John M. Kilcoyne
Attorney, Agent, or Firm—Finnegan, Henderson, Farabow, Garrett & Dunner

[57] ABSTRACT

The fact that Lycorine can be used for suppression of the immune system of mammals is described. Lycorine is therefore suitable for the therapy of autoimmune diseases, immune complex diseases and allergic and rheumatic conditions and for prophylaxis against transplant rejections.

3 Claims, No Drawings

USE OF LYCORINE AS AN IMMUNOSUPPRESSOR

The invention relates to the use of the pharmacologically active substance lycorine or its salts as a suppressor of the immune system in mammals.

The following structure is described for lycorine (Merck Index, 9th edition):

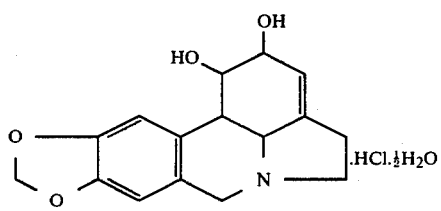

Lycorine can be isolated from extracts of *Crinum pratense* (*Amaryllidaceae*).

The immune system of mammals can be divided into a humoral and a cellular part, the interactions of which are responsible for immunological defense. The function of the immume system is to eliminate substances foreign to the body, such as microorganisms or tumor cells, which can impair the functioning of an organism. However, there are conditions which necessitate influencing of the immunity status of an organism in the sense of suppression. An example of this is the case of an humoral and/or cellular immunological reaction of an organism against its endogeneous tissue. This phenomenon, described as autoimmunity or autoaggressiveness, can cause severe damage to the organism.

Other examples of an undesirable or even harmful effect of the immune system on the organism are immune complex diseases and allergic and rheumatic conditions. In the case of organ transplants, it is necessary to suppress the immunological rejection reaction of the recipient in order to guarantee the survival of the transplanted organ.

In all the cases described above, the reactivity of the immune system must be suppressed by suitable measures. In order to achieve this, the organism is treated with ionizing radiation, with antibodies against lymphatic tissue or with chemical substances (chemical immunosuppressors).

It has now been found, surprisingly, that lycorine hydrochloride hemihydrate can suppress the immune reaction in mammals in amounts of 2.5–20 mg/kg of body weight (in vivo reactions) and the reaction of immunologically competent cells obtained from mice and humans (in vitro reactions) in concentrations of 0.1–100 μg/ml. The concentrations which lead to immunosuppression were significantly below the dosages recognized as toxic and are suitable for the treatment of diseases which have been caused by the immune system and for the prophylaxis of transplant rejections.

This substance suppressed the activity of mouse macrophages in vivo and in cell cultures (in vitro) and the functioning of lymphocytes from mice and humans in cell cultures (in vitro).

The invention accordingly relates to the use of lycorine as an immunosuppressor.

The effective immunosuppressant dosage is in the range from 2.5 to 20 mg/kg of body weight. Solutions or suspensions of the active compound in a pharmaceutically acceptable formulation, preferably buffered aqueous solutions, are suitable for parenteral, in particular intravenous, administration.

The effect of the substance on the immune response in mice and humans in selected standard in vivo and in vitro test methods which, as is known, are used for the evaluation of immunosuppressors is illustrated by way of example below.

EXAMPLE 1

Action of lycorine on macrophage activity in vitro

Female NMRI mice (18–20 g) were sacrificed and the macrophages were removed from the abdominal cavity. The macrophages were then cultured in Petri dishes at 37° C. in an atmosphere containing 5 ml of $CO_2$/100 ml. After 3 hours, the floating cells were removed by washing. Lycorine was then added to the macrophages in concentrations of 50–400 μg/ml and the mixture was left to stand for 24 hours. The activation state was measured with the aid of chemiluminescence, the relative light units (RLU) being integrated for 15 minutes. The action of lycorine both on the non-activated (−zymosan) and on the zymosan-activated (+zymosan) macrophages was measured.

TABLE 1

| Action of lycorine on macrophage chemiluminescence in vitro | | |
|---|---|---|
| Lycorine | Chemiluminescence RLU/15 minutes | |
| μg/ml of test batch | − zymosan | + zymosan |
| 0 | 701 ± 120 | 5435 ± 233 |
| 50 | 655 ± 75 | 4636 ± 201 |
| 100 | 443 ± 17 | 2510 ± 14 |
| 200 | 219 ± 38 | 1083 ± 166 |
| 400 | 142 ± 39 | 741 ± 167 |

Table 1 shows that the macrophage activity after incubation with the substance in vitro was considerably reduced, this applying both to the non-stimulated (−zymosan) and to the in vitro-stimulated (+zymosan) macrophages.

EXAMPLE 2

Activity of mouse macrophages after administration of lycorine in vivo

Lycorine hydrochloride hemihydrate was administered intravenously in concentrations of 2.5–20 mg/kg to female NMRI mice (18–20 g). The controls received the same volume of the solvent (physiologically buffered saline solution, pH 7.2). 3 days later, the mice were sacrificed and the macrophages were taken from their abdominal cavity. The macrophages were transferred to plastic dishes and were cultured for 3 hours at 37° C. in an atmosphere containing 5 ml of $CO_2$/100 ml. At the end of this period, the floating cells were removed by washing. Determination of the activity with the aid of chemiluminescence, as described in Example 1, was carried out on one portion of the cells. The second portion of the cells was cultured for a further 16 hours by the method described above and, after this period, the amount of lysosomal hydrolases (N-acetyl-β-D-glucosaminidase) released was measured in the supernatant.

TABLE 2

| Lycorine mg/kg i.v. | Activity of mouse macrophages following administration of lycorine in vivo | | | |
|---|---|---|---|---|
| | Enzyme release mU/ml N—acetylGlu | | Chemiluminescence RLU/15 minutes | |
| | − zymosan | + zymosan | − zymosan | + zymosan |
| 0 | 824 ± 37 | 4786 ± 287 | 2240 ± 358 | 58,900 ± 849 |
| 2.5 | 681 ± 92 | 3748 ± 196 | 1935 ± 35 | 28,750 ± 2331 |
| 5.0 | 473 ± 46 | 2071 ± 149 | 1115 ± 149 | 13,600 ± 2263 |
| 10.0 | 264 ± 57 | 1428 ± 206 | 762 ± 67 | 8,850 ± 1231 |
| 20.0 | 188 + 18 | 542 + 82 | 348 + 39 | 2,105 + 50 |

As can be seen from Table 2, lycorine reduces the activity of macrophages which have been taken from mice treated with lycorine three days previously. This suppression was observed both in the chemiluminescence and in the release of hydrolytic enzymes with and without the addition of zymosan.

EXAMPLE 3

Action of lycorine on mouse spleen lymphocytes producing IgM and IgG antibodies in vitro $10^8$ sheep erythrocytes were administered intravenously to female NMRI mice. 10 days later, the mice were sacrificed and the spleens were removed under sterile conditions and forced through a sieve, a single-cell suspension of spleen lymphocytes thus being prepared. The spleen lymphocytes ($8 \times 10^6$/2 ml) were incubated for 4 days in tissue culture plates together with $5 \times 10^5$ sheep erythrocytes, lycorine being added in a concentration of 0.01–100.0 µg/ml. The control contained no lycorine. The number of spleen cells producing IgM and IgG antibodies was determined with the aid of the known "plaque forming cell" technique (Jerne & Nordin (1963) Science 140, 405).

The amount of plaque forming cells (PFC) indicates the IgM- or IgG-producing cells per $10^6$ lymphocytes.

TABLE 3

| Lycorine | Action of lycorine on mouse spleen lymphocytes producing IgM and IgG antibodies | |
|---|---|---|
| | Plaque forming cells/$10^6$ lymphocytes | |
| µg/ml of test batch | IgM | IgG |
| 0 | 957 ± 300 | 221 ± 259 |
| 0.01 | 856 ± 139 | 116 ± 45 |
| 0.1 | 799 ± 335 | 48 ± 24 |
| 1.0 | 5 ± 1 | 9 ± 5 |
| 10.0 | 3 ± 2 | 11 ± 4 |
| 100.0 | 3 + 1 | 2 + 2 |

As can be seen from Table 3, total inhibition both of the spleen lymphocytes which produce IgG-antibodies and those which produce IgM-antibodies was observed at concentrations greater than 1.0 µg/ml. 50% inhibition (IC$_{50}$) was achieved with about 0.25 µg/ml in the case of IgM and about 0.015 µg/ml in the case of IgG.

EXAMPLE 4

Action of lycorine on mitogen-stimulated proliferation of human lymphocytes

Lymphocytes were obtained from peripheral human blood by differential centrifugation (dextran, Ficoll). The lymphocytes were then incubated for 2 days in microtitration plates ($3 \times 10^4$ lymphocytes/200 µl) together with the mitogen phytohemagglutinin (PHA, 5 µg/ml) and lycorine in concentrations of 0.1–100 µg/ml. Radioactive thymidine ($^{14}$C) was then added and incubation was continued for 16 hours. Free $^{14}$C-thymidine in the supernatant was then removed from the cells in a cell harvester, and the radioactivity incorporated into the cells was determined as a measure of the lymphocyte proliferation. Parallel lymphocytes without mitogen and without lycorine served as controls. The stimulation index was determined as follows:

$$\text{Stimulation index} = \frac{\text{Experimental radioactivity value}}{\text{Control radioactivity value}}$$

A reduction in the stimulation index accordingly denotes a suppression of lymphocyte proliferation.

TABLE 4

| Action of lycorine on mitogen-stimulated proliferation of human lymphocytes in vitro | |
|---|---|
| Lycorine µg/ml of test batch | Stimulation index |
| 0 | 40 |
| 0.1 | 36 |
| 1.0 | 4 |
| 10.0 | 1 |
| 100.0 | 1 |

As can be seen from Table 4, lycorine suppresses mitogen-stimulated proliferation of human lymphocytes. Total suppression was observed at a concentration of 10 µg/ml of lycorine. 50% inhibition (IC$_{50}$) was achieved with about 0.3 µg/ml.

Thus by in vivo and in vitro test methods which can be used for evaluating immunosuppressants, lycorine is capable of reducing the immunological activity of the recipient. Lycorine can therefore be used as a therapeutic agent for autoimmune diseases, immune complex diseases and allergic and rheumatic conditions and for prophylaxis against transplant rejections.

We claim:

1. A process for the suppression of the immune system of a human in need thereof which comprises administering parenterally lycorine or lycorine hydrochloride to said human in an amount effective to suppress the immune system in said human.

2. The process of claim 1 wherein said amount comprises approximately 2.5 to 20 mg/kg of the body weight of said human.

3. The process of claim 1 wherein said lycorine or lycorine hydrochloride is in a pharmaceutically acceptable carrier.

* * * * *